(12) United States Patent
Yanez et al.

(10) Patent No.: US 9,114,394 B2
(45) Date of Patent: Aug. 25, 2015

(54) CONTAINER HOLDER AND CONTAINER CARRIER

(75) Inventors: Antonio Yanez, Salavaux (CH); Fabrice Ummel, Domdidier (CH); Valentin Zehnder, Sugiez (CH)

(73) Assignee: SYMBION MEDICAL SYSTEMS SARL, Avenches (CH)

( * ) Notice: Subject to any disclaimer, the term of this patent is extended or adjusted under 35 U.S.C. 154(b) by 56 days.

(21) Appl. No.: 14/007,050

(22) PCT Filed: Mar. 26, 2012

(86) PCT No.: PCT/EP2012/055338
§ 371 (c)(1),
(2), (4) Date: Nov. 26, 2013

(87) PCT Pub. No.: WO2012/130805
PCT Pub. Date: Oct. 4, 2012

(65) Prior Publication Data
US 2014/0093438 A1    Apr. 3, 2014

(30) Foreign Application Priority Data
Mar. 25, 2011    (EP) ..................................... 11159881

(51) Int. Cl.
*B01L 9/06*  (2006.01)
*B01L 3/00*  (2006.01)
*G01N 35/04*  (2006.01)

(52) U.S. Cl.
CPC . *B01L 9/06* (2013.01); *G01N 35/04* (2013.01); *B01L 3/5082* (2013.01);
(Continued)

(58) Field of Classification Search
CPC .............................. B01L 9/06; B01L 2200/023
USPC .................................................. 422/560–562
See application file for complete search history.

(56) References Cited

U.S. PATENT DOCUMENTS 3,680,967 A    8/1972  Engelhardt
5,791,618 A *  8/1998  Lancaster .................. 248/311.2
(Continued)

FOREIGN PATENT DOCUMENTS

CN    2350116 Y      11/1999
CN    101232946 A    7/2008
(Continued)

OTHER PUBLICATIONS

Office Action dated Sep. 2, 2014 cited in corresponding Chinese Patent Application No. 201280024830.7.
International Search Report issued in Application No. PCT/EP2012/055338 dated May 29, 2012.

*Primary Examiner* — Paul Hyun
(74) *Attorney, Agent, or Firm* — Pearne & Gordon LLP

(57) ABSTRACT

Container holder suitable for receiving and holding a container, the container holder including a base frame for receiving the container, and at least one supporting member. The at least one supporting member is pivotally mounted on the base frame such as to pivot between a first position in the absence of the container and a second position when the container is received in the base frame. The container holder further includes a displaceable element movably mounted in the base frame such as to move along a predetermined distance that is proportional to the pivotal angle of the at least one supporting member. A displacement sensor is responsive to the predetermined distance of the displaceable element such as to at least determine the diameter of the container when received in the container holder.

13 Claims, 5 Drawing Sheets

(52) U.S. Cl.
CPC ..... *B01L 2200/023* (2013.01); *B01L 2300/023* (2013.01); *B01L 2300/0627* (2013.01); *B01L 2300/0832* (2013.01); *B65G 2201/0258* (2013.01); *G01N 2035/0493* (2013.01)

(56) References Cited

U.S. PATENT DOCUMENTS

| | | | |
|---|---|---|---|
| 6,274,092 B1* | 8/2001 | Itoh | 422/562 |
| 6,843,397 B2* | 1/2005 | Then et al. | 224/552 |
| 6,971,506 B2* | 12/2005 | Hassinen et al. | 198/803.14 |
| 7,485,264 B2* | 2/2009 | Itoh | 422/562 |
| 7,874,535 B2* | 1/2011 | Ogura | 248/311.2 |
| 2005/0207945 A1 | 9/2005 | Itoh | |
| 2010/0089803 A1 | 4/2010 | Lavi | |

FOREIGN PATENT DOCUMENTS

| | | |
|---|---|---|
| EP | 0 471 980 B1 | 2/1992 |
| EP | 0 589 528 B1 | 3/1994 |
| EP | 1 353 183 B1 | 10/2003 |
| WO | 2008/043394 A1 | 4/2008 |
| WO | 2008/067846 A1 | 6/2008 |

* cited by examiner

CONTAINER HOLDER AND CONTAINER CARRIER

FIELD OF THE INVENTION

The present invention relates to a container holder suitable for receiving and holding a container and a container carrier comprising a plurality of the inventive container holder.

DESCRIPTION OF RELATED ART

Wide varieties of automated chemical analyzers are known in the art and are widely used in hospitals, clinics, and research laboratories. A particularly popular example of such a device is the multi-channel type of analyzer in which a series of different tests are performed simultaneously and in parallel with one another. The typical multi-channel analyzer generally utilizes liquid or solid reagents to react with a particular constituent present in a sample to result in a change in transmissibility, absorption, color, photo-optical characteristic or other colligative electrical or physical property of the sample. In conjunction with the multi-channel analyzer, a photo-optical system and electro chemical detector means are employed to determine the rate of reaction, or concentration of the constituent in the sample, and the like. Such chemical analyzers can include analyzers for performing agglutination assays such as that involved in immunohematology.

The usual method employed for performing these photometric procedures is to place a portion or aliquot of the sample solution in a small cell, tube, or cuvette provided with transparent walls, and then to interpose the sample solution between a light source and a photosensitive detecting element or to flow the sample past sensors. In order to perform multiple tests simultaneously on each sample most contemporary multi-channel analyzers utilize a number of small sample aliquots taken from a larger sample volume or specimen originally supplied to the machine. These larger sample specimens are stored and manipulated in cells or tubes of varying size and configuration, the most common being round elongate sample or test tubes, while others include rectangular or square cells and alternative configurations. This form of individualized sample processing avoids the problem of cross-contamination of samples which could occur with the earlier flow-through type of analyzers.

Although multi-channel automated analyzers have received wide acceptance, there are certain drawbacks associated with their use. For example, to provide precise and accurate handling of the sample tubes it is necessary to position and align the tubes within the apparatus accurately so that the various sample aliquots may be automatically and consistently removed as needed. Additionally, in order to correlate the multiple test results properly with the appropriate samples an accurate identification and tracking system must be utilized. As a result, a variety of specialized sample cells and identification means have been developed in the art. Unfortunately, the majority are machine-specific, which limits the applicability of the particular analyzer to those samples which are packaged in the specific sample tubes or cells. Alternatively, some analyzers provide for the use of adapters for sample cells other than the one machine-specific design, which adapters unfortunately, can be clumsy and time-consuming to use. Also, relatively highly-trained personnel are required to operate these conventional analysis machines effectively, as a mistake in their operation can render entire sample runs useless.

It is known to mount sample tubes in a tube container in an analyzer, the container having a well for each tube. Examples are described in U.S. Pat. No. 3,680,967 and in EP0471980.

In U.S. Pat. No. 3,680,967, pairs of spring fingers in each well are used to grip a tube, but no attempt is made to determine the tube diameter, since apparently only one diameter is contemplated.

Documents EP0589528 and WO2008067846 disclose a device for holding a tube container and determining its diameter. More particularly, WO2008067846 discloses a container gripper comprising a main frame and gripper fingers movable between an open position and a closed position. The container gripper is provided with a finger displacement detecting sensor which detects the instantaneous position of the gripper fingers. The disclosed finger detecting sensor is based on a Hall effect assembly such as a Hall effect sensor or on an optical encoder. EP0589528 discloses an apparatus for measuring the diameter of sample tubes held in a sample tube container having a plurality of well portions for each tube. Each well portion comprises a pair of fingers for holding the sample tube and sensing means for senses the distance between the ends of the fingers being spaced apart when the sample tube is held in the sample tube container. The sensing means comprises a conventional electromagnetic radiation emitter and receiver, such as an infrared detector.

Here however, the diameter measurement is based on measuring the relative displacement of the fingers and any misalignment of the fingers may cause inaccurate diameter measurement.

EP1353183 discloses a container holding device comprising holding members for holding the container with an elastic holding force. The container holding device also comprises a pair of freely rotatable rollers mounted on a pair of shafts extending opposite to the holding members. The distance between the rollers, determined by the diameter of the container, determine the degree of opening of the holding members. This device is complex since it requires many moving parts.

BRIEF SUMMARY OF THE INVENTION

An object of the present invention is to provide a container holder which is able to detect the presence of a container in the container holder when the container holder receives a container, hold it firmly when the container is received, and determine its diameter.

It is another aim of the present invention to create a rack comprising a plurality of containers, with which the diameter of the container can be determined.

According to the invention, these aims are achieved by means of a container holder and a container carrier comprising a plurality of the inventive container holder according to the independent claims.

These aims are also achieved by a container holder according to the preamble of the independent claims, characterized in that said at least one supporting member is pivotally mounted on the base frame such as to pivot between first position in the absence of container and a second position when the container is received in the base frame;

in that the container holder further comprises a displaceable element movably mounted in the base frame and connected to a lower end of the supporting member by a force transmitting connection such as to move along a predetermined distance that is proportional to the pivotal angle of said at least one supporting member; and in that a displacement sensor responsive to the predetermined distance of the displaceable element such as to determine at least its diameter when received in the container holder.

In preferred embodiments, the displaceable element is a flanged or teethed element and the said at least one supporting member is pivotally mounted on the base frame by a rivet or a swivel. Preferably, the displaceable element can be moveably mounted on a pin with a spring.

A lateral recess or a hole in the upper surface can be provided in the base frame to accommodate the supporting member.

Preferably, said at least one supporting member holds the container in said second position and the container holder can have three supporting members equally spaced around the base frame. Furthermore, the container holder can comprise a notification unit for notifying when the container is received in the base frame.

Advantageously, the displacement sensor or another sensor can be arranged to detect the presence of a container when is received in the container holder and further comprising a notification unit connected to said sensor for indicating when the container is received in the base frame. The notification unit can be a luminous element disposed in a top portion of the base frame, in the vicinity to the central aperture. The luminous element can emit in single or plural colors to notify on the status of the container when on the base frame.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
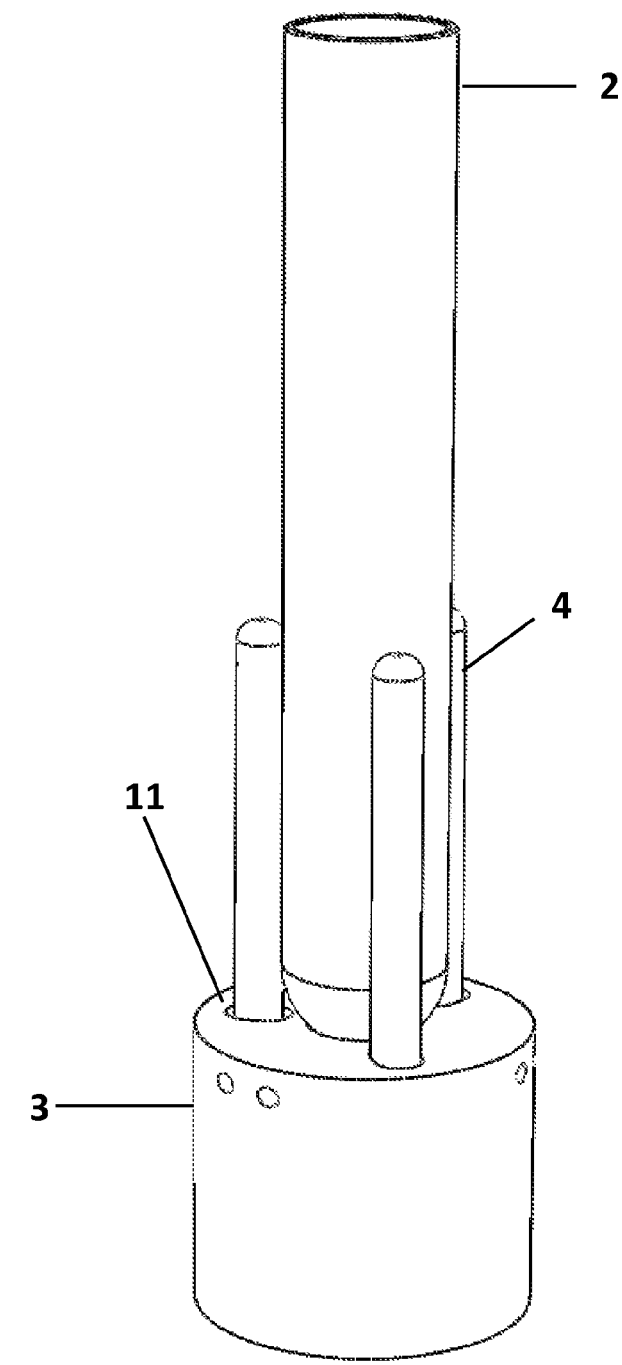
FIG. 1 shows a general view of a first embodiment of an inventive container holder with a container.
Figure 2:
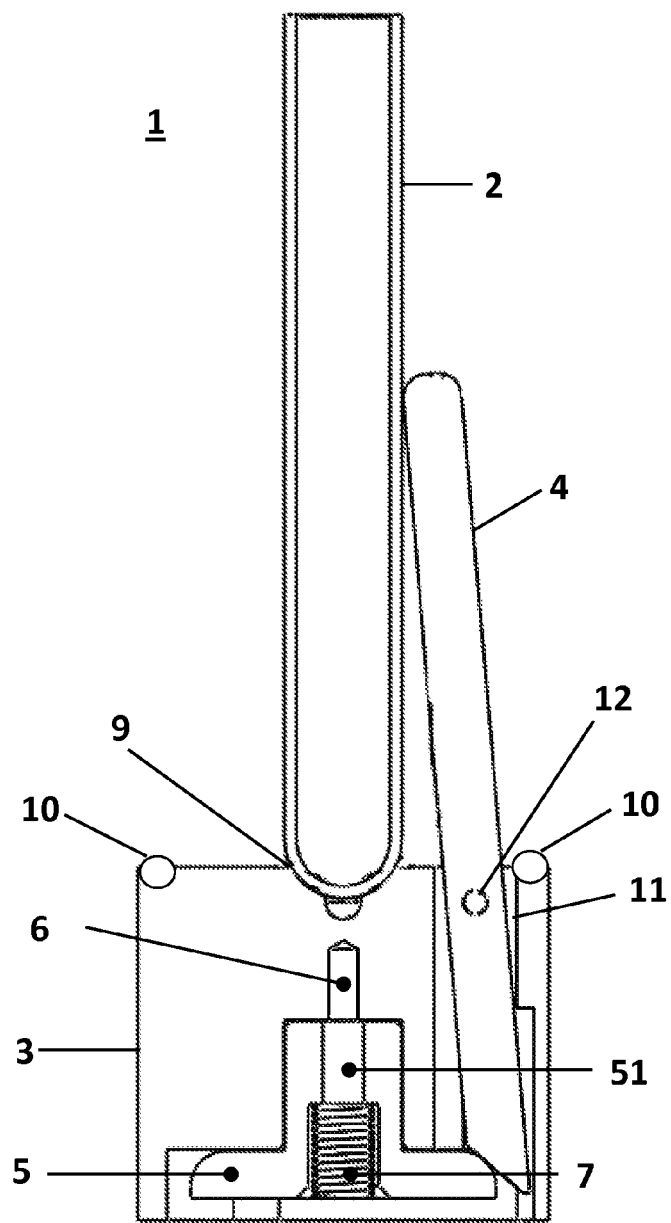
FIG. 2 shows a cut through an inventive container holder with a container having a first diameter.
Figure 3:
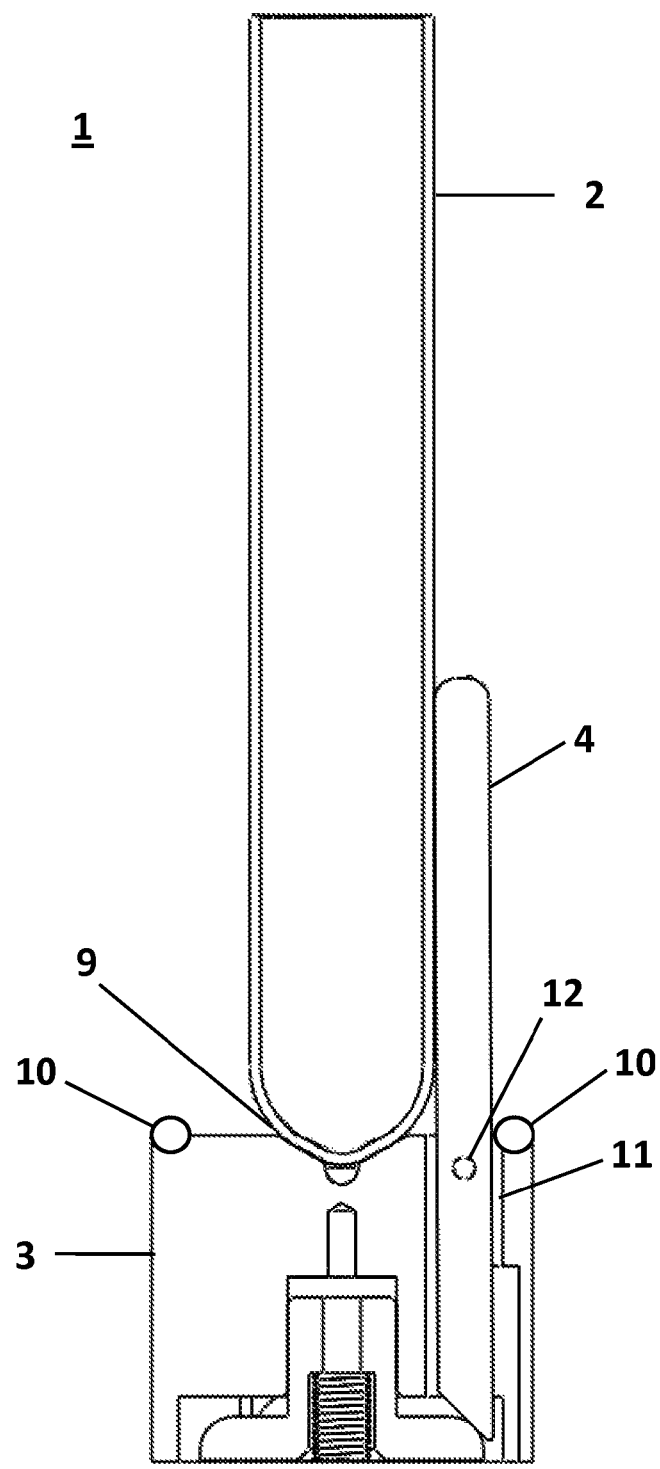
FIG. 3 shows a cut through an inventive container holder with a container having a second diameter smaller than the first diameter shown in FIG. 2.

FIG. 1 shows a general view of a first embodiment of an inventive container holder 1, which is suitable for receiving and holding a container 2 such as to mount the container 2 in an analyzer system (not represented). The container holder 1 is equipped on a lower end with a base frame 3 for receiving and holding said container 2. For this reason a central aperture 9 is provided on the upper surface of the base frame 3. FIG. 2 and FIG. 3 are showing a cross-section view of the container holder 1 with two different diameters of the container 2.

Furthermore said container holder 1 comprises one or more supporting members 4, which are pivotally mounted on the base frame 3. The number of supporting members 4 can however vary and be chosen according to the special embodiment. In one embodiment, the supporting members 4 are equally distributed on the circumference on top of the base frame 3 so that the can stabilize or hold the received containers 2. As they are pivotally mounted part of the supporting members 4 can be seen above the base frame 3 and part is at least partly inside said base frame 3. In one embodiment on the circumference of the base frame 3 there are lateral vertical apertures, recesses or slits 11. The supporting members 4 are fixed inside said recesses 11 just below the upper surface of said base frame 3 in a conventional way such as using a pin 12, rivet, etc., such as to pivot about said pin 12. In another embodiment, there are simply holes 11 in the upper surface of the base frame 3 in which the supporting members 4 are mounted.

As the supporting members 4 are pivotally mounted, they can pivot between first (or open) position and a second (or closed) position. The supporting members 4 are in the absence of a container 2 in said first position. The supporting members 4 are in said second position when the container 2 is received in the base frame 3. In this second position said at least one supporting member 4 holds the container 2.

Inside said base frame 3 is arranged a displaceable or moveable member or element 5, which is movably mounted with a central part on a pin 6. The element 5 has a flange for the force transmitting connection to the lower end of the supporting member 4. Below the central part and inside the displaceable element 5 is disposed a compressed spring 7, which naturally would move the displaceable element 5 up on said pin 6. The flange of the element 5 is provided on circumferentially around the central part. As the element 5 is in force transmitting contact with the lower end of the supporting members 4, the members 4 pivot according to the displacement of said element 5 moving along said pin 6. When a container 2 is inserted the lower end of the supporting member 4 displaces the element 5 against the force exercised by the spring 7. In that way the element 5 moves along a predetermined distance that is proportional to the pivotal angle of said supporting members 4.

Finally, a first sensor, or a displacement sensor (indicated by numeral 16 in FIG. 6), is responsive to the predetermined distance of the element 5 detects the presence of the container 2. As the displacement is proportional to the pivotal angle of said at least one supporting member 4, it is as well proportional to the diameter of the container 2 when it is received in the container holder 1. As an example FIG. 2 and FIG. 3 are showing containers 2 with two different diameters.

The container holder 1 may further comprise a notification unit 10 for notifying when the container 2 is received in the base frame 3. The notification unit 10 can be adapted to produce an optical, audible signal, or other sensorial signal. Preferably, the notification unit comprises a luminous element 10, for example, a light-emitting diode (LED), disposed in a top portion of the base frame 3, in the vicinity to the central aperture 9. In the embodiment of FIGS. 2 and 3, the luminous element 10 is ring-shaped and disposed concentric with the central aperture 9. However, the luminous element 10 can have any other shape, such as a disk shape, and be disposed on any positions on the base frame 3 where an operator can easily visually it.

The luminous element 10 can emit in a single color or plural colors adapted to notify on the status of the container 2 when on the base frame 3. For example, the luminous element 10 can emit in green to notify that the series of different tests have been performed and the container 2 can be removed from the container holder 1, in red to notify the series of tests is not finished and the container 2 should not be removed from the container holder 1, and in yellow to notify a possible error in the series of tests. In the latter case, a sensor (not represented) may detect a clogging pipette, a fluid volume shortage, or any other abnormality in a treatment and analysis operation may be identified in the analyzer system. Alternatively, the luminous element 10 can by a single color LED and the status of the container 2 can be notified by making the LED blinks according to a different blinking pattern depending on the status.

Figure 4:
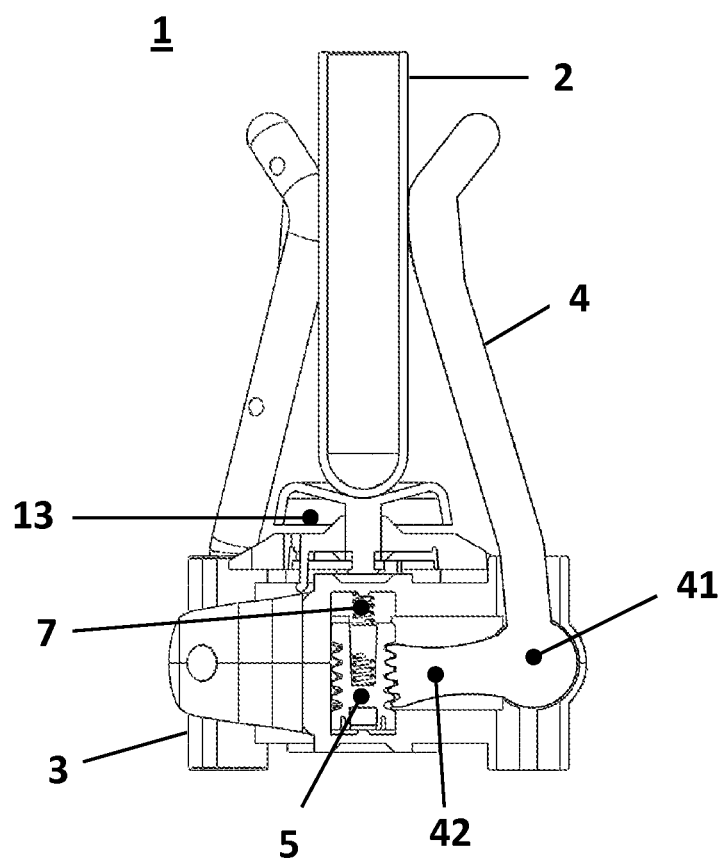
FIG. 4 shows a general view of a second embodiment of an inventive container holder with a container.

FIG. 4 shows a general view of a second embodiment of an inventive container holder with a container. In this embodiment a seat 13 is provided, which can slightly pressed down, once the container 2 is received. In this embodiment the supporting members 4 are hinged by a swivel 41 inside the base frame 3. To the second end of the swivel 41 is connected a teethed rack 42. Due to the swivel 41 said teethed rack 42 moves up or down by moving said supporting members 4. In this embodiment, the displaceable element 5, again mounted on spring 7, has counterpart teeth to the teeth of the teethed rack 42. In this way, the element 5 will simply follow the movement up and down of the teethed rack 42, whenever the supporting members 4 are moved. The force transmitting connection is therefore realized by connecting both elements 5, 42 by the teeth. However, in this embodiment the direction of movement will be opposite to the movement of the first embodiment. Therefore in fact the spring 7 is mounted above the element 5 pressing the element 5 down. As for the first embodiment the displacement sensor 16, shown in detail in FIG. 6, will be responsive to the predetermined distance of the element 5 such as to detect the presence of the container 2 and determine its diameter when received in the container holder 1.

In fact in the framework of the present invention any force transmitting connecting between the moveable element 5 and the lower end of the supporting members 4 could be used.

Figure 5:
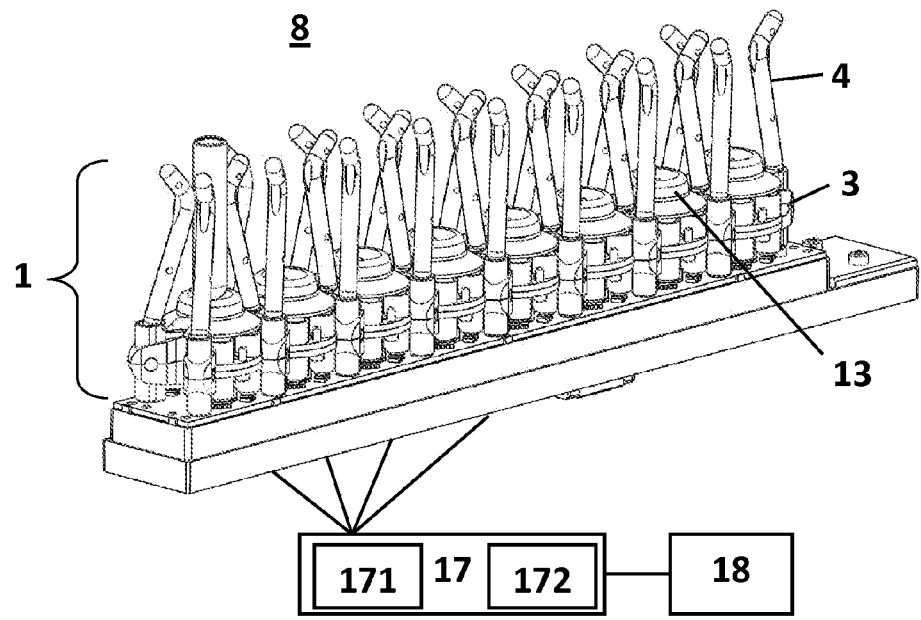
FIG. 5 shows a container carrier comprising a plurality of the inventive container holder, a communication unit and an automated analyzer.

The present invention relates as well to a container carrier 8 suitable to be received in an automated chemical analyzer comprising a plurality of the inventive container holder 1. This embodiment can be seen in FIG. 5 where container carrier 8 comprises an array of the plurality of container holders 1, each container holders capable of receiving a container 2. In the embodiment, the container holders 1 are represented with three supporting members 4 equally spaced around the base frame 3.

Containers 2 with different diameters can be received in the different container holders 1 of the container carrier 8, said at least one supporting member 4 of each container holder 1 being displaced in accordance to the diameter of the container 2. The container carrier 8 disclosed herein is then able to detect the presence of a container 2 in any one of its container holders 1 and determine the container's diameter.

The container carrier 8 is connected via a communication unit 17 to a controlling unit 18. The communication unit 17 receives by use of a receiving unit 171 information about the status of each of the containers 2 comprised in any one of the container holder 1 of the container carrier 8. The following transmission of the information to the controlling unit 18 can be made in any way, e.g. by NFC communication, WiFi, Bluetooth, or by simply integrating the unit into the carrier 8 and connecting it by cables. A suitable transmission unit 172 will be provided in the communication unit 17. This received information can be used to control the notification unit 10 on the container holders 1 as a function, for example, of the advancement of the series of tests. Furthermore, the container carrier 8 can include a storing unit (not shown) for storing the displacement sensor signal information and/or the information from the controlling unit 18. This arrangement allows automatically inputting the information about the container holders 1 comprising a container 2 and the diameter of the corresponding containers 2. Thus, there is no need to manually provide this information to the analyzer.

Figure 6:
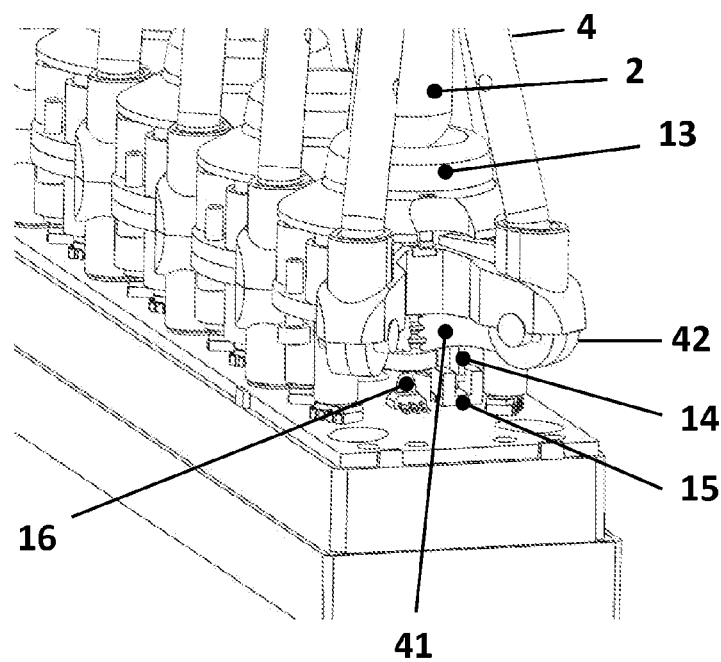
FIG. 6 shows a detail of a container holder with different presence and displacement sensors.

FIG. 6 shows a detail of a container holder 1 including different presence and displacement sensors. The seat 13 is connected via a connected element 14 to a second sensor, or a presence sensor 15. The presence of a container 2 is detected, when the connected element 14 moves slightly. The presence sensor 15 can be for a Hall effect sensor or any other suitable sensor. Alternatively, the displacement sensor 16 provides a sensor signal containing the information relative to the presence of the container 2 in the container holder 1 and its diameter. Again, the sensor 16 can be for a Hall effect sensor or any other suitable sensor. The container carrier 8 can also comprise a communication unit to communicate between the container carrier 8 and the automated analyzer.

REFERENCE NUMBERS AND SYMBOLS

1 Container holder
2 Container
3 Base frame
4 Supporting member
41 Swivel
42 Teethed rack
5 Element
6 Pin
7 Spring
8 Container carrier
9 Central aperture
10 Notification unit
11 Vertical recess, hole
12 Pin
13 Seat
14 Connecting element
15 Presence sensor
16 Displacement sensor
17 Communication unit
171 Receiving unit of unit 17
172 Transmitting unit of unit 17
18 Controlling unit

What is claimed is:

1. Container holder suitable for receiving and holding a container, said container having a diameter, said container holder comprising:
   a base frame for receiving said container having a diameter; and
   at least one supporting member;
   said at least one supporting member being pivotally mounted on the base frame such as to pivot between a first position in the absence of the container and a second position when the container is received in the base frame;
   the container holder further comprising a displaceable element movably mounted in the base frame and connected to a lower end of the supporting member by a force transmitting connection such as to move along a predetermined distance that is proportional to the pivotal angle of said at least one supporting member; and
   a displacement sensor responsive to the predetermined distance of the displaceable element such as to determine at least the diameter of the container when received in the container holder.

2. Container holder according to claim 1, wherein said force transmitting connection is a flange of said displaceable element connected to the lower end of the supporting member.

3. Container holder according to claim 1, wherein said force transmitting connection is a teethed element connected to a teethed rack at the lower end of the supporting member.

4. Container holder according to claim 1, wherein said at least one supporting member is pivotally mounted on the base frame by a rivet or a swivel.

5. Container holder according to claim 1, wherein the displaceable element is moveably mounted on a pin with a spring.

6. Container holder according to claim 1, wherein a lateral recess or a hole is provided in an upper surface of the base frame to accommodate the supporting member.

7. Container holder according to claim 1, wherein said at least one supporting member holds the container in said second position.

8. Container holder according to claim 1 with three supporting members equally spaced around the base frame.

9. Container holder according to claim 1, wherein the displacement sensor or another sensor detects the presence of a container when it is received in the container holder and further comprising a notification unit connected to said sensor for indicating when the container is received in the base frame.

10. Container holder according to claim 9, wherein said notification unit is a luminous element disposed in a top portion of the base frame, in the vicinity to a central aperture.

11. Container holder according to claim 10, wherein said luminous element can emit a single or plural color(s) to indicate the status of the container when on the base frame.

12. A container carrier suitable to be received in an automated chemical analyzer and comprising a plurality of container holders, each container holder being suitable for receiving and holding a container having a diameter and comprising: a base frame for receiving said container and at least one supporting member; said at least one supporting member being pivotally mounted on the base frame such as to pivot between a first position in the absence of container and a second position when the container is received in the base frame; each container holder further comprising a displaceable element movably mounted in the base frame and connected to a lower end of the supporting member by a force transmitting connection such as to move along a predetermined distance that is proportional to the pivotal angle of said at least one supporting member; and a displacement sensor responsive to the predetermined distance of the displaceable element such as to determine at least the diameter of the container when received in the container holder.

13. Container carrier according to claim 12, further comprising a communication unit, wherein said communication unit comprises a transmission unit for transmitting sensor signals provided by each of the displacement sensors to a controlling unit.

* * * * *